(12) United States Patent
Wein et al.

(10) Patent No.: US 9,764,178 B1
(45) Date of Patent: Sep. 19, 2017

(54) ELECTRICITY GENERATING SYSTEM

(71) Applicants: Michael Wein, Houston, TX (US);
Phillip Sarofim, Houston, TX (US)

(72) Inventors: Michael Wein, Houston, TX (US);
Phillip Sarofim, Houston, TX (US)

( * ) Notice: Subject to any disclaimer, the term of this patent is extended or adjusted under 35 U.S.C. 154(b) by 0 days.

(21) Appl. No.: 15/193,752

(22) Filed: Jun. 27, 2016

Related U.S. Application Data

(60) Provisional application No. 62/185,384, filed on Jun. 26, 2015.

(51) Int. Cl.
| | | |
|---|---|---|
| *A63B 24/00* | (2006.01) | |
| *A63B 21/005* | (2006.01) | |
| *H02K 7/18* | (2006.01) | |
| *H02K 11/27* | (2016.01) | |

(52) U.S. Cl.
CPC ...... *A63B 21/0055* (2015.10); *A63B 24/0059* (2013.01); *A63B 24/0062* (2013.01); *A63B 24/0087* (2013.01); *H02K 7/1861* (2013.01); *H02K 11/27* (2016.01)

(58) Field of Classification Search
CPC . A63B 24/00; A63B 24/0062; A63B 24/0087; A63B 24/0059; A63B 21/0055; H02K 7/1861; H02K 11/27
See application file for complete search history.

(56) References Cited

U.S. PATENT DOCUMENTS

| | | | | |
|---|---|---|---|---|
| 8,446,275 | B2* | 5/2013 | Utter, II | A61B 5/0205 340/539.12 |
| 8,485,944 | B2* | 7/2013 | Drazan | A63B 21/0053 482/1 |
| 8,647,240 | B2* | 2/2014 | Heidecke | A63B 21/0053 482/4 |
| 9,126,076 | B2* | 9/2015 | Liang | A63B 21/0053 |
| 9,283,421 | B2* | 3/2016 | Duval | A63B 21/0053 |
| 9,352,188 | B2* | 5/2016 | Astilean | A63B 22/02 |
| 9,457,217 | B2* | 10/2016 | Yin | F03G 5/00 |

OTHER PUBLICATIONS

Gibson, Tom; "These Exercise Machines Turn Your Sweat into Electricity"; Jun. 21, 2011.

* cited by examiner

*Primary Examiner* — Glenn Richman
(74) *Attorney, Agent, or Firm* — Rao DeBoer Osterrieder, PLLC; Dileep P. Rao

(57) ABSTRACT

An electricity generating system using fitness equipment, wherein the fitness equipment can be used to produce electricity with a generator. The electricity produced can be transferred from the generator to a splitter. A controller can be used to receive identifications and decisions on transfer of the produced electricity from a fitness center. The controller can be used to track in real time electricity produced as watts or as amperage associated with a user identification, a fitness class identification, or an administrator identification input less than 10 minutes before the electricity is produced or at a preset time, which can then transfer in real time energy credits equivalent to electricity produced or transfer produced electricity to a destination designed in the a user decision, a fitness class decision, or an administrator decision.

11 Claims, 3 Drawing Sheets

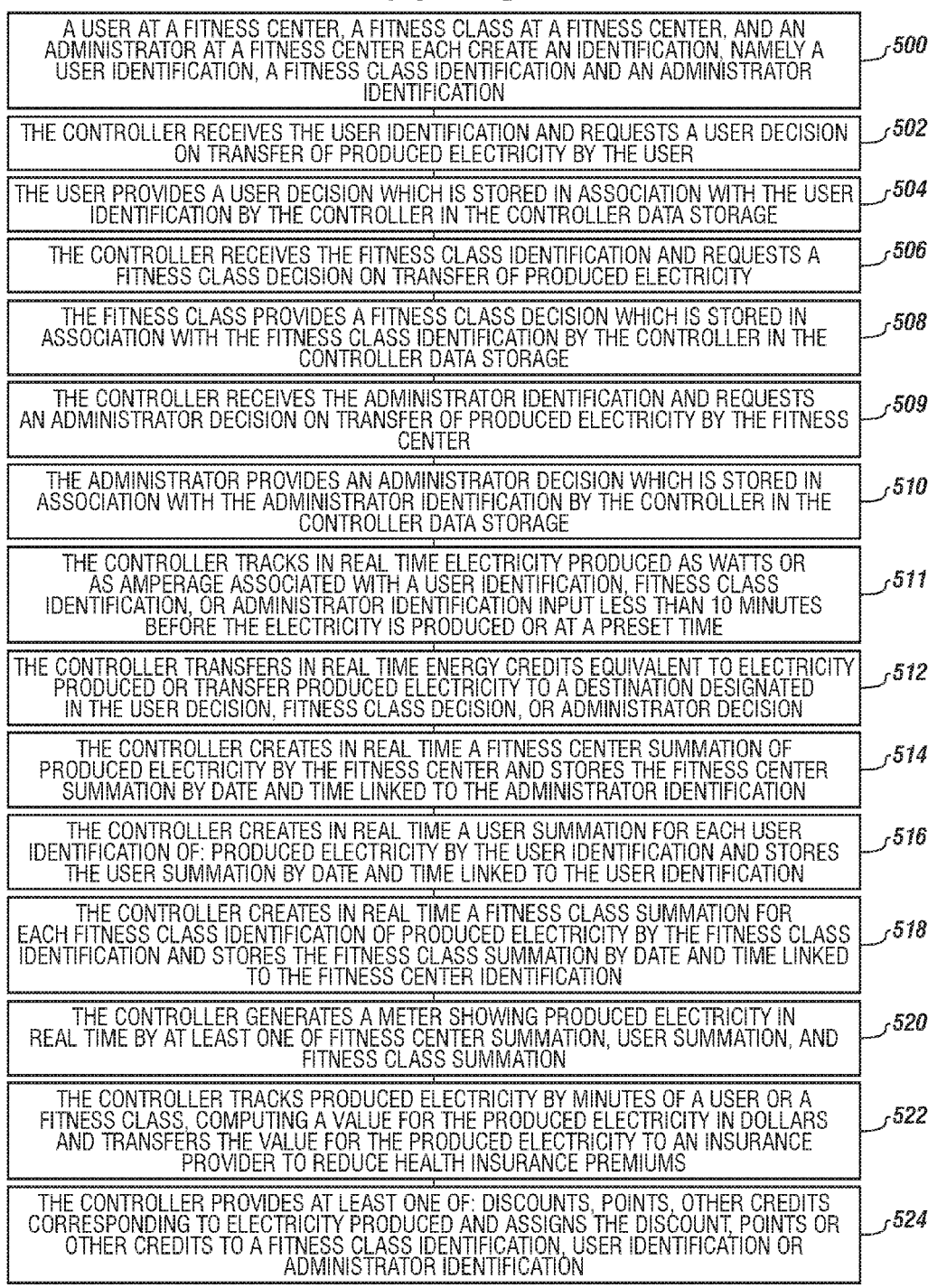

ELECTRICITY GENERATING SYSTEM

CROSS REFERENCE TO RELATED APPLICATION

The current application claims priority to and the benefit of U.S. Provisional Patent Application Ser. No. 62/185,384 filed on Jun. 26, 2015, entitled "ELECTRICITY GENERATING SYSTEM". This reference is hereby incorporated in its entirety.

FIELD

The present embodiments generally relate to an electric generating system.

BACKGROUND

A need exists for a net neutral workout experience wherein users are able to generate electricity when working out, neutralizing their carbon footprint by adding electricity to the power grid.

A need exists for capturing energy from fitness centers either on an individual basis or a class basis or for the entire facility.

A need has existed to enable individuals and groups of individuals to direct the transfer of produced energy in real time to destinations of their choosing.

The present embodiments meet these needs.

BRIEF DESCRIPTION OF THE DRAWINGS

The detailed description will be better understood in conjunction with the accompanying drawings as follows:

FIG. 3 shows an exemplary method by which the system operates according to one or more embodiments.

Figure 1:
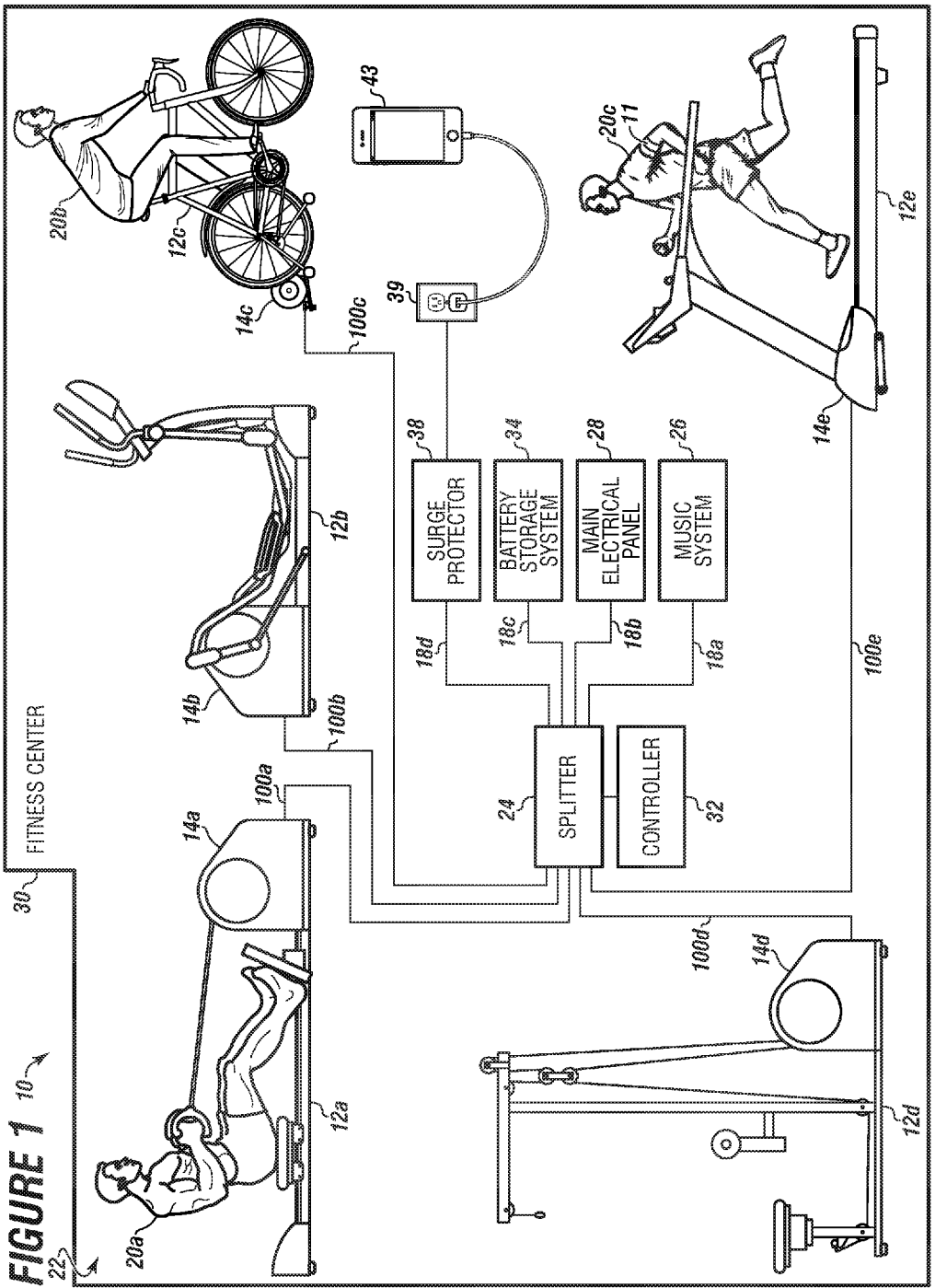
FIG. 1 is a diagram of an electricity producing system according to one or more embodiments.

The present embodiments are detailed below with reference to the listed Figures.

DETAILED DESCRIPTION OF THE EMBODIMENTS

Before explaining the present system in detail, it is to be understood that the system is not limited to the particular embodiments and that it can be practiced or carried out in various ways.

The present embodiments generally relate to an electric generating system.

The electric generating system can comprise a plurality of fitness equipment and a generator connected to the fitness equipment for producing electricity as the fitness equipment is operated by at least one user of a fitness class.

The electric generating system can comprise a splitter to transfer a first portion of produced electricity to a music system and a second portion of produced electricity to the main electrical panel of the fitness center.

The electric generating system can comprise a controller to monitor electricity generation from the generator and to direct the electricity selectively using the splitter based on a decision of at least one user in the fitness class.

Individual pieces of exercise equipment, such as stationary bicycles, rowing machines and elliptical machines can all generate electricity by a user when operated.

The electric generating system can enable individual users, or groups of individual users to generate electricity, track that generated electricity, transfer the electricity or the value equivalent of electricity to destinations of the individual's choosing, the group's choosing, or the fitness center's choosing.

With this electric generating system, gyms can promote themselves as charity friendly or rebate friendly, enabling users or groups of users to decide if they personally want to use the produced power right then, if they personally want a credit for produced power, or if they personally want to donate their produced power to a charity.

In embodiments, the electric generating system with fitness equipment can be connected in parallel, wherein each piece of fitness equipment produces electricity with a generator.

The electric generating system can include transferring the electricity produced to an electronic splitter, wherein a portion of the produced electricity can be transferred to a music system, a main electrical panel, a battery storage system, or combinations thereof.

A controller can be connected to the electronic splitter and can be configured to receive an administrator identification and an administrator decision, a user identification and a user decision, a fitness class identification and fitness class decision on how to transfer the produced electricity from the fitness center.

The controller can be configured to track in real time electricity produced in watts or as amperage associated with the administrator identification, the user identification, or the fitness class identification, which can be inputted in about 10 minutes or less before the electricity is produced or at a preset time.

The controller can be configured to transfer in real time energy credits equivalent to electricity produced or transfer produced electricity to a destination designed in the administrator decision, the user decision, the fitness class decision, or combinations thereof.

The controller can be configured to create in real time a fitness center summation of produced electricity by the fitness center and store the fitness summation by date and time, which can then be linked to the administrator identification.

The controller can be configured to create in real time a user summation for each user identification of produced electricity by the user identification and store the user summation by date and time, which can then be linked to the user identification.

The controller can be configured to create in real time a fitness class summation for each fitness class identification of produced electricity by the fitness class identification and store the fitness class summation by date and time, which can then be linked to the fitness center identification.

The controller can be configured to generate a meter showing produced electricity in real time by the fitness center summation, the user summation, the fitness class summation, and combinations thereof.

In embodiments, competitions can be held and each user can compete against another user, a group or a class for a preset amount of time. The competitions can be timed events where one user can compete against another user or group of users. In embodiments, the user or a group of users that produce the most electricity can receive a prize, such as a cash incentive, a trophy, a reward, or be able to designate where the accumulated produced electricity is to be spent. In embodiments, the competitions can be a single event, a monthly event, or a group of events. In embodiments, the competitions can be a 30 minute class, or can be a total number of electricity produced over a period of time, such as during a month, a day or a year.

Turning now to the Figures, FIG. 1 is a diagram of an electricity producing system according to one or more embodiments The electric generating system 10 can include a plurality of fitness equipment 12a, 12b, 12c, 12d and 12e, which can be operated by at least one user 20a, 20b, and 20c to generate electricity.

In embodiments, the at least one user can wear a kinetic energy storage device and by doing sit ups, running, lifting weights, the at least one user can also produce electricity, which can be directly stored into a kinetic energy storage device 11. The kinetic energy storage device can download stored energy into the system when plugged in.

The plurality of fitness equipment can include, but is not limited to a rowing machine, an elliptical machine, a stationary bicycle, a spin cycle, weight lifting equipment, a treadmill, or combinations thereof, which can all generate electricity with the system.

In embodiments, the plurality of fitness equipment can be a plurality of spin cycles, a plurality of treadmills, a plurality of elliptical machines, a plurality of rowing machines, a plurality of mechanized weight lifting machines or combinations thereof.

Each piece of fitness equipment can use a generator 14a, 14b, 14c, 14d, and 14e, which can be built in the fitness equipment or an installed aftermarket. The kinetic energy storage device 11 does not need a generator, but can include a generator in embodiments.

In embodiments, the generator can be, but is not limited to a flywheel, a spinning wheel, a system of connected pulleys, an elastic resistance device or combinations thereof.

In embodiments, the kinetic energy device can have a kinetic spring wound mechanism akin to kinetic ROLEX® watch.

Each generator for each piece of fitness equipment can produce at least 100 watts of power when operated by a user per hour and up to 350 watts in an hour of fitness activity. The kinetic energy generator can produce variable energy depending on what type of exercise is performed with the kinetic energy device.

Each generator 14a, 14b, 14c, 14d, and 14e can connect to a splitter 24, which in embodiments, can be electronic, and can be configured to receive produced electricity 100a, 100b, 100c, 100d and 100e and to transfer that produced electricity. Although not shown in this Figure (due to proximity) the kinetic energy generator 11 can also connect to the splitter, such as through a plug in port.

The splitter 24 can be controlled and operated by a controller 32.

The controller can be a microprocessor, a computer, programmable logic board, an electrical flow meter that monitors the watts, or combinations thereof.

The controller can have computer instructions to a instruct a controller processor to identify the fitness center, identify the members, track generated electricity, store and implement where to transfer produced electricity, and provide alarms to at least one client device indicating individuals have failed to produce enough power or have exceeded preset goals. The controller can create priority groupings for transfer of the power, ensuring the most important pieces of equipment at the center are powered first off grid.

The splitter 24 can be configured to transfer a first portion of produced electricity 18a to a music system 26 of the fitness center 30. In embodiments, the splitter can transfer a few watts of power produced by an entire fitness class, such as from 1000 watts to 4000 watts, to operate a music system with receiver, transmitter and speakers into the fitness class.

The splitter 24 can be configured to transfer a second portion of produced electricity 18b to a main electrical panel 28 of the fitness center 30. In embodiments, the splitter can transfer a few watts of power produced by an entire fitness class, such as from 1000 watts to 4000 watts, to the main electrical panel of the fitness center 30 where the quantity can be tracked and applied to powering washing machines, appliances, and lights of the fitness class.

The splitter 24 can be configured to transfer a third portion of produced electricity 18c to a battery storage system 34 of the fitness center 30. In embodiments, the splitter can transfer a few watts of power produced by an entire fitness class, such as from 1000 watts to 4000, to the battery storage system of the fitness center 30 to keep the fitness center off grid, lowering its carbon footprint.

The splitter 24 can be configured to transfer a fourth portion of produced electricity 18d to a surge protector 38, which can connect to a power outlet 39, enabling at least one client device 43, but additionally a plurality of client devices to be charged by electricity transmitted to the power outlet from the fitness class. In embodiments, the splitter can transfer a few watts of power produced by an individual, such as 5.5 watts for a 30 minute work out with the kinetic device to 4000 watt for 10 people working a spin class.

The at least one client device 43 can be a cellular phone, a MP3 player, an IPAD®, a smart device, such as a smart watch, a tablet computer, a computer, an additional device with a processor and bidirectional communication, or combinations thereof.

In embodiments, the electric generating system can produce from 5 watts of power to 10,000 watts of power per hour at an active fitness center to operate difference devices, which can include the music system with receiver, transmitter and speakers, lights, ice machines, computers, and washers and dryers of the fitness center.

In embodiments, the kinetic energy device can use weights, mats and exercise classes to produce kinetic energy as a group of fitness members.

In embodiments, the produced electricity can be about 100 watts of power per hour of exercise by a single person, from 10 watts to 20 watts less of power per hour by a single child, from 10 watts to 30 watts of power per hour by a handicapped person, or can exceed 5000 watts of power per hour of exercise by a professional athlete.

Figure 2:
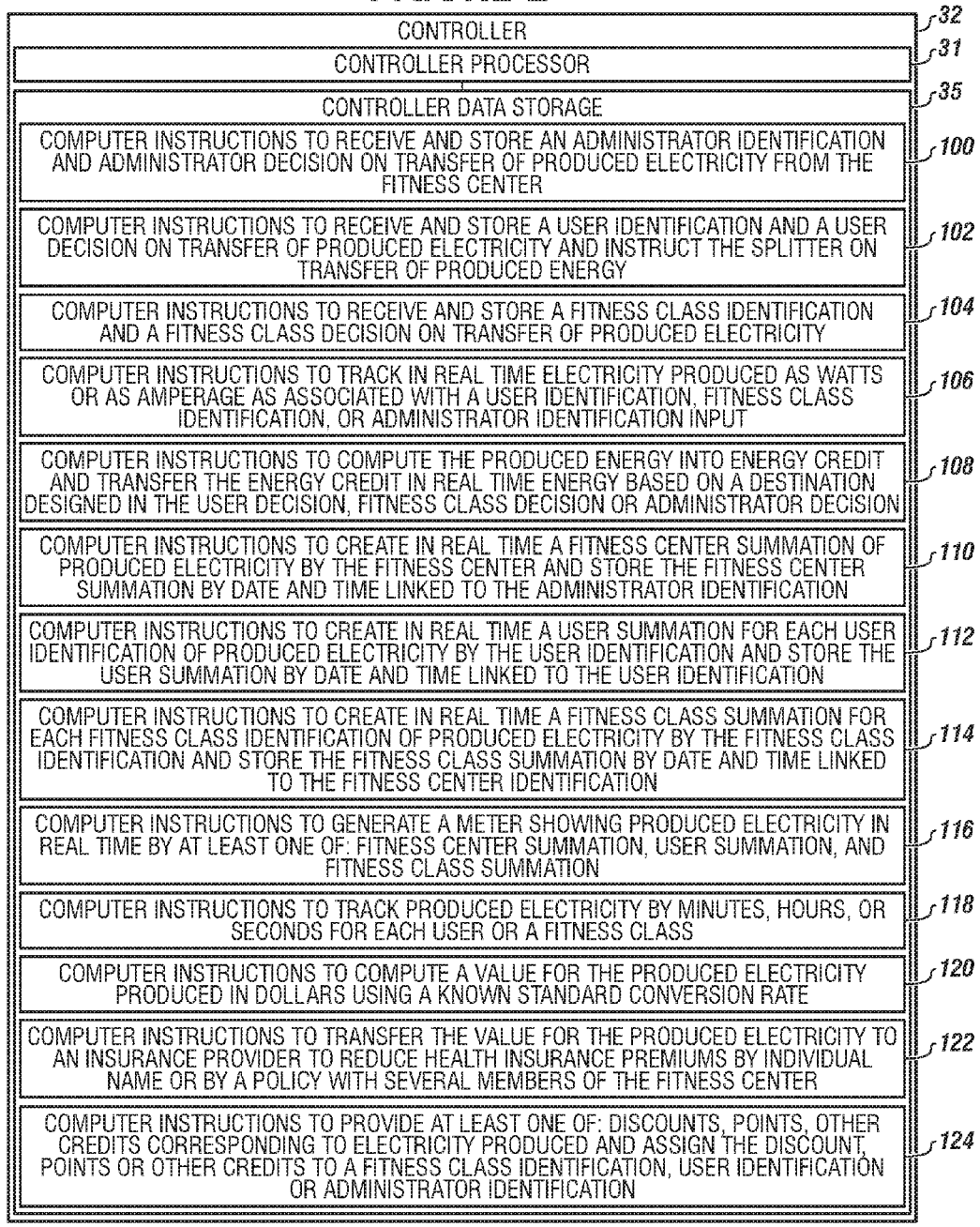
FIG. 2 is a diagram of a controller usable with the electricity producing system accordingly to one or more embodiments.

FIG. 2 is a diagram of the controller usable with the electricity producing system accordingly to one or more embodiments.

The controller 32 can contain a controller processor 31 and controller data storage 35. The data storage 35 can contain a plurality of computer instructions to instruct the controller processor 31 to do various tasks.

The term "data storage" as used herein refers to a non-transitory computer readable medium, such as a hard disk drive, solid state drive, flash drive, tape drive, and the like. The term "non-transitory computer readable medium" excludes any transitory signals but includes any non-transitory data storage circuitry, e.g., buffers, cache, and queues, within transceivers of transitory signals.

In embodiments, the data storage 35 can contain computer instructions 100 to receive and store an administrator identification and administrator decision on transfer of produced electricity from the fitness center.

For example, the administrator can be President Bob Smith at the Bob's Gym who deices to transfer all produced power to the Bob's Gym as an administrator decision.

The data storage 35 can contain computer instructions 102 to receive and store a user identification and a user decision on transfer of produced electricity and instruct the splitter on transfer of produced energy.

For example, the user can be Michael, a spinning bike user and his decision is only 50 percent of his power goes to the fitness center and 50 percent of his power is transferred into energy credit to be donated to charity, MEALS ON WHEELS® for their use.

The data storage 35 can contain computer instructions 104 to receive and store a fitness class identification and a fitness class decision on transfer of produced electricity.

For Example, Michael's favorite spinning bike class can have a class identification Mike's Party Group and the class decision is that all electricity is donated to a charity.

In embodiments, the data storage can have a filter to make the class decision overrule the individual decision, when the individual uses a certain class.

The data storage 35 can contain computer instructions 106 to track in real time electricity produced as watts or as amperage of associated with a user identification, fitness class identification, or administrator identification input.

In embodiments, the tracking in real time can begin no less than 10 minutes before the electricity is produced or at a preset time.

The data storage 35 can contain computer instructions 108 to compute the produced energy into energy credit and transfer the energy credit in real time energy based on a destination designed in the user decision, fitness class decision or administrator decision.

In embodiments, the destination can be a charity, the fitness center, the individual's electricity account with the power company, a work address, a home address, or another type of address.

The data storage 35 can contain computer instructions 110 to create in real time a fitness center summation of produced electricity by the fitness center and store the fitness center summation by date and time linked to the administrator identification.

For example, all the electricity produced can be totaled and stored for electricity, which can be controlled under the administrator decision.

The data storage 35 can contain computer instructions 112 to create in real time a user summation for each user identification of produced electricity by the user identification and store the user summation by date and time linked to the user identification.

For example, all the electricity produced can be totaled and stored for electricity, which can be controlled under the user decision.

The data storage 35 can contain computer instructions 114 to create in real time a fitness class summation for each fitness class identification of produced electricity by the fitness class identification and store the fitness class summation by date and time linked to the fitness center identification.

For example, all the electricity produced can be totaled and stored for electricity, which can be controlled under the class decision.

The data storage 35 can contain computer instructions 116 to generate a meter showing produced electricity in real time by at least one of: fitness center summation, user summation, and fitness class summation.

For example, all the electricity produced can be totaled and presented on a digital meter with a date and time on a display near the entrance to the fitness center.

The data storage 35 can contain computer instructions 118 to track produced electricity by minutes, hours, or seconds for each user or a fitness class.

The data storage 35 can contain computer instructions 120 to compute a value for the produced electricity produced in dollars using a known standard conversion rate.

For example, the daily electricity rates for households as indicated in the WALL STREET JOURNAL®.

The data storage 35 can contain computer instructions 122 to transfer the value for the produced electricity to an insurance provider to reduce health insurance premiums by individual name or by a policy with several members of the fitness center.

The data storage 35 can contain computer instructions 124 to provide at least one of: discounts, points, other credits corresponding to electricity produced and assign the discount, points or other credits to a fitness class identification, user identification or administrator identification.

For example, the points can be used to buy clothing or additional services at the fitness center as a reward for transferring electricity to the fitness center. The points can be awarded by a charity that receives the power credits, such as points redeemable for tickets to a baseball game.

FIG. 3 shows an exemplary method by which the system operates according to one or more embodiments.

The method can include a user at a fitness center, a fitness class at a fitness center, and an administrator at a fitness center each create an identification, namely a user identification, a fitness class identification and an administrator identification, illustrated in box 500.

The method can include the controller receives the user identification and requests a user decision on transfer of produced electricity by the user, illustrated in box 502.

The method can include the user provides a user decision which is stored in association with the user identification by the controller in controller data storage, illustrated by box 504.

The method can include the controller receives the fitness class identification and requests a fitness class decision on transfer or produced electricity, illustrated by box 506.

The method can include the fitness class provides a fitness class decision which is stored in association with the fitness class identification by the controller in controller data storage, illustrated by box 508.

The method can include the controller receives the administrator identification and requests an administrator decision on transfer of produced electricity by the fitness center, illustrated by box 509.

The method can include the administrator provides an administrator decision which is stored in association with the administrator identification by the controller in controller data storage, illustrated by box 510.

The method can include the controller tracks in real time electricity produced as watts or as amperage associated with a user identification, fitness class identification, or administrator identification input less than 10 minutes before the electricity is produced or at a preset time, illustrated by box 511.

The method can include the controller transfer in real time energy credits equivalent to electricity produced or transfer produced electricity to a destination designed in the user decision, fitness class decision, or administrator decision, illustrated by box 512.

The method can include the controller creates in real time a fitness center summation of produced electricity by the fitness center and store the fitness center summation by date and time linked to the administrator identification, illustrated by box 514.

The method can include the controller creates in real time a user summation for each user identification of produced electricity by the user identification and store the user summation by date and time linked to the user identification, illustrated by box 516.

The method can include the controller creates in real time a fitness class summation for each fitness class identification of produced electricity by the fitness class identification and store the fitness class summation by date and time linked to the fitness center identification, illustrated by box 518.

The method can include the controller generates a meter showing produced electricity in real time by at least one of: fitness center summation, user summation, and fitness class summation, illustrated by box 520.

The method can include the controller tracks produced electricity by minutes of a user or a fitness class, computing a value for the produced electricity in dollars and transfers the value for the produced electricity to an insurance provider to reduce health insurance premiums, illustrated by box 522.

The method can include the controller provides at least one of: discounts, points, other credits corresponding to electricity produced and assign the discount, points or other credits to a fitness class identification, user identification or administrator identification.

In another embodiment, the electric generating system can include a method for generating electricity that uses a client device connected to a network to connect from a fitness center to an energy management center.

The method can include that each user of the fitness center using the client device create a user profile with user identification, a fitness class profile with a fitness class identification for each fitness class at the fitness center, and for each administrator an administrator profile with an administrator identification and then storing the profiles and identifications in an administrator data storage in communication with the client device.

The method can include presenting a selection of destinations using the client device to each user with a user identification, fitness class with a fitness identification, and administrator with an administrator identification, wherein the selection of destinations include at least one of: energy credit equivalents to energy produced at the fitness center and actual electricity produced at the fitness center.

The method can include transmitting from the client device the selection of destinations for each user, fitness class and administrator and storing the selection in the user profile, fitness class profile and administrator profile in the administrative data storage.

The method can include connecting fitness equipment to individual generators, enabling each user to produce electricity with an individual piece of fitness equipment.

The method can include connecting the fitness equipment to the energy management center to receive and store generated electricity as each user or fitness class starts a routine, enabling each user to log in with a user identification or a fitness class identification.

The method can include using the energy management center to track in real time electricity produced in watts or in amps associated with each user identification and each fitness class identification and store produced energy in a battery storage system.

The method can include transferring from the energy management center in real time either energy credits equivalent to electricity produced by user identification or fitness class identification or transferring produced electricity to a destination designed in the user profile, fitness class profile, or administrator profile.

The method can include creating in real time a fitness center summation of produced electricity by the fitness center and storing the fitness center summation by date and time linked to the administrator identification.

The method can include creating in real time a user summation for each user identification of produced electricity by the user identification and storing the user summation by date and time.

The method can include creating in real time a fitness class summation for each fitness class with fitness class identification of produced electricity and storing the fitness class summation by date and time.

The method can include generating a meter graphically representing at least one of: the fitness center summation and the user summation.

The method can include tracking produced electricity by minutes of a user or by minutes of all users in a fitness class.

The method can include computing a value for the produced electricity in dollars using a same day traded rate for energy.

The method can include transferring the energy credit value for the produced electricity to an insurance provider to reduce health insurance premiums of the user or member of the fitness class.

In embodiments, the system can accumulate energy credits and can designate energy credits to one or more sources.

As an example, Benjamin goes regularly to a cycling class at his local gym and sometimes he uses the elliptical machines by himself. In the group setting, such as a cycling class, the system can designate a portion to each of the participants in the group. The portions can be equal for each individual or can be performance-based portions. The system can aggregate energy credits as part of the group and add to total accumulated energy credits based on Benjamin's solo gym activity also.

In embodiments, the energy credits can go somewhere other than to the user. In embodiments, the energy credits can be designated to a final recipient based on individual decisions, on group decisions or on some other decision criteria.

In embodiments, the energy decision criteria can be changed in real time by an entity, such as a user, an administrator, a class, a group, a dispersed group, a remote group, a facility, or combinations thereof.

As an example, the instructions can be for the Mad Dawg Fitness gym to decide to donate energy credits to a charity or foundations, such as HABITAT FOR HUMANITY®.

In embodiments, the decision criteria can be determined by an individual or a class. In another example, an administrator at the fitness facility can make the decision on where to transfer at least a portion of the energy credits, such as back to the gym where they were created to run the lights, music, TVs, projectors or other equipment requiring energy to run.

In an embodiment, the energy credits can be in the form of a rebate, a credit or another unit of measure.

Getting a group of people together in an environment such as a fitness class to make a collective decision on where energy credits go is different than an individual decision on how to utilize power. One reason this is different is that you can form classes around common goals or common causes and transfer energy credits to those organizations.

In embodiments, energy credits can be donated to a non-profit organization or other destination decided on by the group.

In embodiments, users can be identified by a unique identifier comprising: a user code, a gym card swiped at each machine, a radio frequency identification tag, and a trackable device such that the system can identify when an individual is using a particular machine, how long they are using the machine, how much energy is exerted on the machine and aggregate how many energy credits are accumulated based on this data. The trackable device can be electrically powered, kinetically powered, or powered with any commercially available battery or commercially available powering system.

As an example, Christopher meets Benjamin at the gym and they each work out for an hour. Benjamin spends the entire hour in the cycling class while Christopher uses the fitness equipment working his chest and triceps on a few machines that are actuated with a pulley system. In both cases, they are generating electricity via electromagnetic frequencies actuated by the fitness equipment. The number of energy credits accumulated, however, varies based on the how much power and how much force is exerted on the various forms of fitness equipment.

In embodiments, there can be a display screen that shows the place, the class, the individual, the summation of energy per piece of fitness equipment, and the bigger summation number by day, week, month, class, or combinations thereof.

In an embodiment, the display screen can show up in the class setting, in the fitness facility or in a public setting.

In an embodiment, the display screen can show up on an out-of-class device, such as a cellular phone or other trackable device. In an embodiment, the display screen can know where it is via embedded GPS capabilities. The smart device can communicate where it is to the fitness facility, thereby enabling the fitness facility to track user output on a timed and measured basis.

In another embodiment, the class can take place outside of a fitness facility.

An electronic splitter is a connector that divides an incoming line and distributes it to multiple locations based on decision criteria.

A controller is a generic term for any embedded system that controls one or more of the electrical systems or subsystems.

An electrical flow meter is a measurement device relying on an inductance or impedance bridge or electrical-resistance rod elements to sense, monitor and change flow rate variations.

In an embodiment, kinetic energy storage is a system of converting movement into stored energy.

Flywheel energy storage works by accelerating a rotor or flywheel to a very high speed and maintaining the energy in the system as rotational energy. When energy is extracted from the system, the flywheels rotational speed is reduced as a consequence of the principle of conservation of energy; adding energy to the system correspondingly results in an increase in the speed of the flywheel.

In an embodiment, the flywheel energy storage system uses electricity to accelerate and decelerate the flywheel.

In an embodiment, the flywheel energy storage system uses mechanical energy to accelerate and decelerate the flywheel.

Adding energy to the system correspondingly results in an increase in the speed of the flywheel.

In an embodiment, the flywheel energy storage system is used to absorb or release electrical energy.

In an embodiment, the flywheel energy system can be described as either mechanical, kinetic or inertia batteries.

In an embodiment, the flywheel energy storage system has rotors made of high strength carbon-fiber composites, suspended my magnetic bearings and spinning at speeds from 10.000 to over 50,000 RPMs in a vacuum enclosure.

In an embodiment, the flywheel energy storage system can come up to speed in a matter of minutes, reaching their energy storage capacity more quickly than some other forms of energy storage.

In embodiments, rapid charging of a system can occur in less than 15 minutes.

In embodiments, flywheel energy systems have long lifetimes and last for decades with little or no maintenance.

In embodiments, the energy efficiency of the invention, wherein energy efficient is defined to be a ratio of energy out per energy in of flywheels, also known as round-trip efficiency, can be as high as 90 percent.

In embodiments, energy capacities range from 3 kWh to more than 200 kWh.

In embodiments, the maximum specific energy of a flywheel rotor is dependent on the rotor's geometry and the properties of the material used.

In an embodiment, the rotors can be anisotropic.

In an embodiment, the rotors can be isotropic and made from a single material. In this example, the relationship can be expressed with variables defined as: kinetic energy of the rotor (J), the mass of the rotor (kg), the geometric shape factor of the motor, the tensile strength of the material (Pa), the density of the material (kg/m$^3$).

A generator is a device that converts mechanical energy to electrical energy for use in an external circuit.

The splitter can be a power splitter, a power divider, power combiners or directional couplers. In an embodiment, the splitter couples a defined amount of the electromagnetic power in a transmission line to a port, enabling the signal to be used in another circuit.

A directional coupler only couples power flowing in one direction.

In an embodiment, power entering the output port is coupled to the isolated port but not to the coupled port.

Directional couplers and power dividers provide a signal sample for measurement or monitoring, feedback, combining feeds to and from and separating transmitted and received signals.

A music system is equipment used for amplifying audio to be heard or felt by an audience.

In embodiments an electrical panel is called a distribution board, a panelboard or a breaker panel.

An electrical panel is a component of an electricity supply system that divides an electrical power feed into subsidiary circuits.

In an embodiment, the electrical panel provides a protective fuse or circuit breaker for each circuit in a common enclosure.

In an embodiment, an electrical panel is comprised of: a main switch, at least one residual-current device and a residual current breaker with overcurrent protection.

A battery storage system captures energy produced at one time and saves the energy for use at a later time.

A device that stores energy is sometimes called an accumulator. Accumulators can collect multiple forms of energy including radiation, chemical energy, gravitational potential energy, electrical potential energy, electricity, energy created from elevated or reduced temperature, latent heat energy and kinetic energy.

In an embodiment, energy storage converts energy from forms that are difficult to store to more conveniently or economically storable forms.

Most global energy storage is dominated by pumped hydro power. This invention helps make a new form of energy creation and storage possible.

In an embodiment, the battery storage system can provide short-term energy storage. In another embodiment, the battery storage system can provide long-term energy storage.

In an embodiment, the energy isn't stored directly, but can be used to power daily energy requirements of the facility.

A user summation can be a report generated to aggregate accumulated energy or stored energy credits.

A fitness class summation can be a report generated to aggregate the accumulated energy or stored energy credits created by a class.

A fitness facility summation can be a report generated to aggregate the accumulated energy or stored energy credits created by a gym or fitness facility with multiple pieces of fitness equipment.

In an embodiment, a meter can be an electricity meter, electric meter, electrical meter or energy meter. In an embodiment, the meter can be a device that measures the amount of electric energy consumed or generated.

Electric meters can be used to measure electric energy generated for the purpose of creating energy credits. In embodiments, the meters can be calibrated in billing units, such as the kilowatt hour (kWh). Meters can be read in real time or on a periodic accumulation schedule.

In an embodiment, meters can measure energy accumulation during certain periods. In embodiments, meters can measure the demand of power in some interval.

While these embodiments have been described with emphasis on the embodiments, it should be understood that within the scope of the appended claims, the embodiments might be practiced other than as specifically described herein.

What is claimed is:
1. An electricity generating system comprising:
   a. at least one of: a plurality of fitness equipment connected in parallel and a plurality of kinetic energy storage devices designed to produce and store energy;
   b. at least one generator connected to at least one piece of fitness equipment of the plurality of fitness equipment for producing electricity as the at least one piece of fitness equipment is operated by at least one user;
   c. a splitter configured to receive the produced electricity from the at least one generator and at least one kinetic energy storage device of the plurality of kinetic energy storage devices, if used, and to transfer:
      (i) a first portion of produced electricity to a music system of a fitness center;
      (ii) a second portion of produced electricity to a main electrical panel of the fitness center, and
      (iii) a third portion of produced electricity to a battery storage system of the fitness center; and
   d. a controller in electronic communication with the splitter to:
      (i) receive an administrator identification and an administrator decision on transfer of the produced electricity from the fitness center; and to perform at least one of:
         1. receive a user identification and a user decision on transfer of the produced electricity and instruct the splitter on transfer of the produced energy; and
         2. receive a fitness class identification and a fitness class decision on transfer of the produced electricity;
      (ii) track in real time electricity produced in watts or in amperage associated with the user identification, the fitness class identification, or the administrator identification;
      (iii) transfer in real time energy credits equivalent to the electricity produced or transfer actual produced electricity in real time to a destination designed in the user decision, the fitness class decision, or the administrator decision;
      (iv) create in real time a fitness center summation of the produced electricity by the fitness center and store the fitness center summation by date and time linked to the administrator identification;
      (v) create in real time a user summation for the user identification of the produced electricity by the user identification and store the user summation by date and time linked to the user identification;
      (vi) create in real time a fitness class summation for the fitness class identification of the produced electricity by the fitness class identification and store the fitness class summation by date and time linked to the fitness center identification; and
      (vii) generate a meter for displaying to the at least one user and the fitness center showing the produced electricity in real time using at least one of: the fitness center summation, the user summation, and the fitness class summation.

2. The electricity generating system of claim 1, wherein the at least one piece of fitness equipment comprises at least one of: a plurality of spin cycles, a plurality of stationary bicycles, a plurality of treadmills, a plurality of elliptical machines, a plurality of rowing machines, a plurality of mechanized a plurality of weight lifting machines, or combinations thereof.

3. The electricity generating system of claim 1, wherein the at least one generator is a flywheel, a spinning wheel, a system of connected pulleys, an elastic resistance device, or combinations thereof.

4. The electricity generating system of claim 1, wherein the produced electricity is from 10 watts to 4000 watts of power per hour per person.

5. The electricity generating system of claim 1, wherein the controller is a microprocessor, a computer, a programmable logic board, an electrical flow meter that monitors the watts, or combinations thereof.

6. The electricity generating system of claim 1, comprising a surge protector and a power outlet enabling at least one client device to be recharged using a fourth portion of produced electricity of at least 5 watts.

7. The electricity generating system of claim 6, wherein the at least one client device is a cellular phone, an MP3 player, a tablet computer, a smart device, or combinations thereof.

8. The electricity generating system of claim 1, wherein the controller is further configured to:
   a. track the produced electricity by minutes of the at least one user or a fitness class;
   b. compute a value for the produced electricity in dollars; and c. transfer the value for the produced electricity to an insurance provider to reduce health insurance premiums.

9. The electric generating system of claim 8, wherein the controller is further configured to provide at least one of: discounts, points, credits corresponding to electricity produced and assign the discount, points or other credits to the user identification, the fitness class identification, or the administrator identification.

10. The electric generating system of claim 9, wherein the controller is further configured to calculate the at least one of: the discounts, the points, the credits corresponding to electricity produced are calculated for a preset amount of time during a competition.

11. A method for generating electricity comprising:
a. using at least one client device connected to a network to connect from a fitness center to an energy management center;
b. using the at least one client device to create a user profile with a user identification for at least one user, a fitness class profile with a fitness class identification for at least one fitness class, and an administrator profile with an administrator identification for at least one administrator and store the user profile, the fitness class profile, and the administrator profile in an administrator data storage in communication with the at least one client device;
c. presenting a selection of destinations using the at least one client device to the at least one user with the user identification, the at least one fitness class with the fitness identification, and the at least one administrator with the administrator identification, for at least one of:
(i) energy credits equivalent to energy produced at the fitness center, and
(ii) actual electricity produced at the fitness center;
d. transmitting from the at least one client device the selection of destinations for the at least one user, the at least one fitness class, and the at least one administrator and storing the selection in the user profile, the fitness class profile, and the administrator profile in the administrative data storage;
e. connecting fitness equipment to individual generators, enabling the at least one user to produce electricity with an individual piece of fitness equipment;
f. connecting the fitness equipment to the energy management center to receive and store generated electricity;
g. enabling the at least one user to log in with the user identification or the fitness class identification as the at least one user or the at least one fitness class starts a routine;
h. using the energy management center to track in real time the electricity produced in watts or in amps associated with the user identification and the fitness class identification and store the produced energy in a battery storage system;
i. transferring from the energy management center in real time either energy credits equivalent to the electricity produced by the user identification or the fitness class identifying or transferring produced electricity to a destination designed in the user profile, the fitness class profile, or the administrator profile;
j. creating in real time a fitness center summation of the produced electricity by the fitness center and storing the fitness center summation by date and time linked to the administrator identification;
k. creating in real time a user summation for the user identification and the fitness class identification of the produced electricity by the user identification and store the user summation by date and time linked to the user identification and the fitness class identification;
l. generating a meter graphically representing at least one of: the fitness center summation and the user summation;
m. tracking the produced electricity by minutes of the at least one user or by minutes of all users in the at last one fitness class;
n. computing a value for the produced electricity in dollars using a same day traded rate for energy; and
o. transferring the value for the produced electricity to an insurance provider to reduce health insurance premiums.

* * * * *